United States Patent [19]

Catalucci

[11] 4,224,446

[45] Sep. 23, 1980

[54] PROCESS FOR THE PRODUCTION OF METHOTREXATE

[75] Inventor: Enrico Catalucci, Arona, Italy

[73] Assignee: Lonza Ltd., Basel, Switzerland

[21] Appl. No.: 926,009

[22] Filed: Jul. 19, 1978

[30] Foreign Application Priority Data

Aug. 12, 1977 [CH] Switzerland ........................ 9894/77

[51] Int. Cl.$^2$ .................. A61K 31/495; C07D 487/04
[52] U.S. Cl. ..................................... 544/257; 544/260; 424/250
[58] Field of Search ............................... 544/257, 260

[56] References Cited

U.S. PATENT DOCUMENTS 3,989,703  11/1976  Duvaz ............................ 260/251.5

FOREIGN PATENT DOCUMENTS 55885  12/1970  Romania .

OTHER PUBLICATIONS

Seeger et al., J. Am. Chem. Soc., 71, 1753 (1949).
Suster et al., J. Medic Chem., 17, 758 (1974).
Baugh et al., J. Org. Chem., 29, 3610 (1964).
Piper et al., J. Heter. Chem., 11, 279, (1974).
Chaykowsky, M., J. Medic. Chem., 17, 1212 (1974).
Mauthnew et al., J. Org. Chem. 40, 3447, (1975).
Adamson, R., et al., "Arch. Int. Pharmacodyn," 1965, 153, No. 1-2, p. 87.

*Primary Examiner*—Donald G. Daus
*Assistant Examiner*—L. Jones
*Attorney, Agent, or Firm*—Fisher, Christen & Sabol

[57] ABSTRACT

Process for the production of methotrexate, which is N[p-([(2,4-diamino-6-pteridyl)-methyl]-N$^{10}$-methylamino)-benzoyl]-L-glutamic acid. The process includes converting 1,1-dichloroacetone with 2,4,5,6-tetraaminopyrimidine in the presence of sodium bisulfite at a constant pH between 3.5 and 5 and at a temperature between 10° and 100° C. The resultant 2,4-diamino-6-methylpteridine is converted in a reaction medium with bromide. 0.3 to 1.0 ml of bromine is used per 1.0 g of the 2,4-diamino-6-methylpteridine. The 2,4-diamino-6-bromo methyl pteridine is converted with p-(N-methyl)-aminobenzoyl-L-glutamic acid or a salt thereof in a polar reaction medium into methoxtrexate.

14 Claims, No Drawings

PROCESS FOR THE PRODUCTION OF METHOTREXATE

BACKGROUND OF THE INVENTION

1. Field of This Invention

This invention relates to a process for the production of methotrexate, which is N[p-([(2,4-diamino-6-pteridyl)-methyl]N$^{10}$-methylamino)-benzoyl]-L-glutamic acid.

2. Prior Art

The only production method, which is known to have been used on an industrial scale, rests on a condensation of 2,4,5,6-tetraaminopyrimidine with 2,3-dibromopropanol and p-(N-methyl)-aminobenzoyl-glutaminic acid [see D. R. Seeger et al., J. Am. Chem. Soc. 71, 1753 (1949)]. However, the yield in such case is very low and lies below 6 percent. The product is contaminated with pteridines to such a point that one cannot practically succeed in producing pure methotrexate in an economical manner.

The use of 1,1,3-trichloroacetone instead of 2,3-dibromopropanol produces no essential advantages [see D. C. Suster et al., J. Medic Chemistry 17, 758 (1974)].

An attempt has also been made to synthetize methotrexate by way of 2,4-diamino-6-hydroxymethyl-pteridine. See the following process scheme:

In a further step, the hydroxymethylpteridine can be converted with thionylchloride into 2,4-diamino-6-chloromethyl pteridine. Because of the sensitivity of the hydroxymethylpteridine, the reaction with SOCl$_2$ takes a very bad course. The resultant contaminated chloromethylpteridine produces a crude methotrexate in a 7 percent yield (content 60 percent). [See I. N. Duvaz et al., U.S. Pat. No. 3,989,703 (1976)].

The production of the bromomethylpteridine from the 6-hydroxymethylpteridine at about 36 percent yield takes a somewhat selective course. However, the necessity of the use of triphenylphosphine dibromide in a four fold stoichiometric excess as the bromation reagent makes any industrial use of the process more difficult [see J. R. Piper et al., J. Heter. Chem. 11, 279, (1974)].

The halomethylpteridines for their part can then be converted with p-(methyl)-aminobenzyl glutamic acid into methotrexate.

Finally, a way via pyrazine systems is known [see M. Chaykowsky, J. Medic, Chem. 17, 1212 (1974)].

Diketene and malonitrile are converted in two steps into 2-amino-3-cyano-5-chloromethylpyrazine-1-oxide and the latter is converted in the presence of phosphorus chloride into 2-amino-3-cyano-5-chloromethyl pyrazine. The latter is converted with p-(N-methyl)-aminobenzoyl-L-glutamic acid and is changed with guanidine in a cyclization reaction into methotrexate.

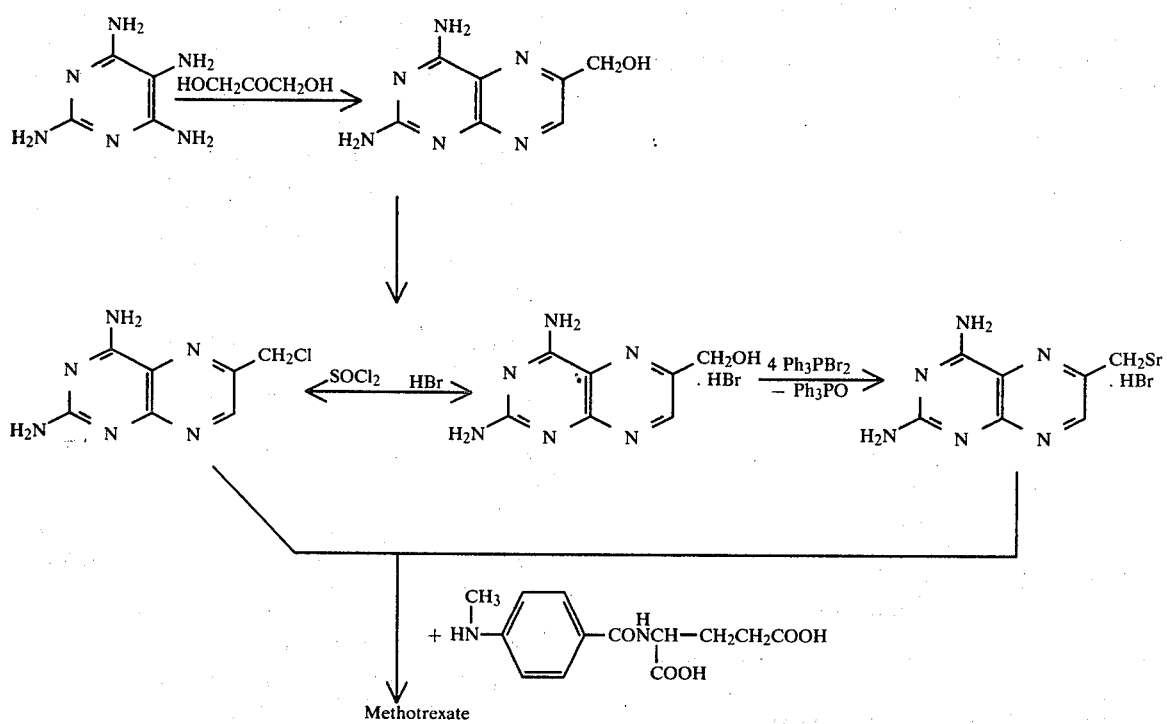

The 6-hydroxymethylpteridine may be obtained in accordance with (C. M. Baugh et al., J. Org. Chem. 29, 3610 (1964)) by a complicated and expensive process from 2,4,5,6-tetraaminopyrimidine and dihydroxyacetone in a 50 to 60 percent raw product yield. The easily-accessible tetraaminopyrimidine sulfate at the same time has to first be converted by means of BaCl$_2$ into its chloride. Furthermore, equimolar quantities of the very expensive, cysteine are used for the cyclization reaction. (According to applicant's own experiments, the product contains about ⅓rd undesirable 6-methylpteridine.)

The great disadvantage of these systems lies in the fact that in the case of the last condensation step, an unavoidable total racemization of the glutamic acid part takes place. Such is very disadvantageous because the D-form of the methotrexate is much less active in the inhibition of tumors [for example, see H. G. Mauthner et al., J. Org. Chem. 40, 3447 (1975)].

BROAD DESCRIPTION OF THIS INVENTION

An object of this invention is to provide a process for the production of methotrexate, which produces pure L-methoxytrexate without complicated purification proceedures, starts out from easily accessible starting materials and continues via simple steps of synthesis which can also be carried out without problems on an industrial scale. Other objects and advantages of this invention are set out herein or are obvious herefrom to one ordinarily skilled in the art.

The objects and advantages of this invention are achieved by the process of this invention.

Methotrexate has the formula:

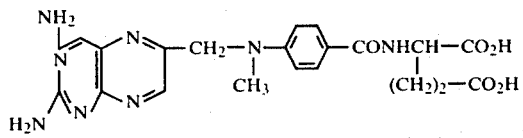

This invention involves a process for the production of methotrexate. The process includes:

(1) converting 1,1-dichloroacetone with 2,4,5,6-tetraaminopyrimidine in the presence of sodium bisulfite at a constant pH of 3.5 to 5 and at a temperature between 10° and 100° C.;

(2) converting the resultant 2,4-diamino-6-methylpteridine with bromide, in a reaction medium, 0.3 to 1.0 ml of the bromide being used per 1.0 g of pteridine compound; and (3) converting the resultant 2,4-diamino-6-bromomethylpteridine with p-(N-methyl)-amino benzoyl-L-glutamic acid or one of its salts in a polar reaction medium to L-methotrexate.

The process of this invention is based on the following series of process steps:

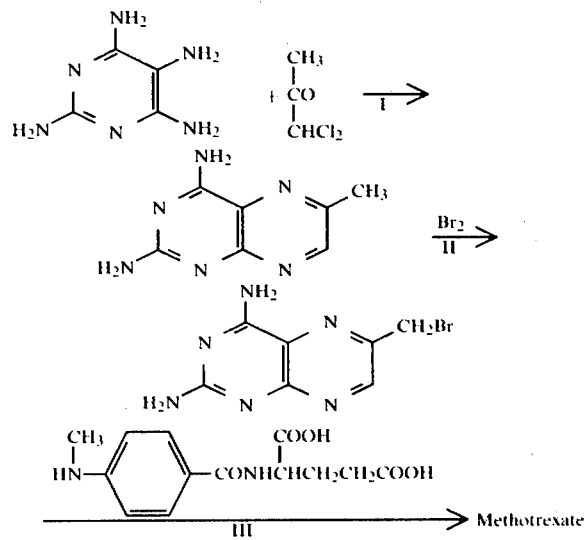

The first step of the process of this invention can be carried out starting out from the 1,1-dichloroacetone, which can be produced from acetone by simple chlorination.

Effectively, the 1,1-dichloroacetone is converted at a temperature, which is preferably 60° to 80° C., with 2,4,5,6-tetraaminopyrididine. 1 to 3 moles, preferably 2 moles of 1,1-dichloroacetone is used per mole of pyridine compound. The conversion is conducted in the presence of 1 to 4 moles, preferably 1.5 to 1.8 mole of sodium bisulfite per mole of pyrimidine at a constant pH which is preferably 4. The pH can be kept constant by addition as needed of a diluted base. Preferably the diluted base is NaOH, NaHCO₃ or NH₄OH in water, wherein 3 to 25 liters, preferably 6 to 8 liters, of water is used. The 2,4-diamino-6-methylpteridine obtained during the reaction in the first step is NMR-pure and is above all free of 7-isomer compounds. The 2,4-diamino-6-methylpteridine can be used in the next step without purification.

In a second step, the conversion to the 6-halogenmethyl pteridine compound takes place.

In an effective embodiment, the 2,4-diamino-6-methylpteridine is converted with bromine at reflux temperature in a reaction medium which is water, 60 percent hydrogen bromide, glacial acetic acid or trifluoro acetic acid. Preferably glacial acetic acid is used as the reaction medium. 7 to 9 liters of reaction medium are used per mole of 2,4-diamino-6-methylpteridine. Preferably 0.7 ml of the bromine is used per 1.0 of the 2,4-diamino-6-methylpteridine.

The reaction product can be isolated as the hydrobromide by concentrating the reaction mix by evaporation. It can be recrystallized from glacial acetic acid. The product contains, according to NMR, certain amounts of methyl-and dibromomethyldiaminopteridine.

The conversion 2,4-diamino-6-bromomethylpteridine into methoxtrexate follows as the third reaction step. The third step can be carried out by converting the 2,4-diamino-6-bromomethylpteridine in a polar solvent, such as water, dimethylformamide, dimethyl acetamide or mixtures thereof, with p-(N-methyl)-aminobenzoyl-L-glutamic acid or the barium salt of p-(N-methyl)-aminobenzoyl-L-glutamic acid in the presence of a soluble base at ambient (room) temperature into methotrexate. Preferably the soluble base is NaOH or NaHCO₃. 10 to 100 parts by weight of the reaction medium is used per part by weight of the reactants. Preferably the polar solvent is a mixture of one volume of water and one volume of dimethylformamide. The methotrexate is obtained in pure form. However, the methotrexate can be purified further by precipitation, corresponding to subsequent requirements.

Examples of other useful polar solvents are dimethyl sulfoxide, ethanol, diethyl sulfoxide, ethyleneglycoldialkylether, formamide, methyl propionamide, sulfolane, N-methyl formamide, dimethyl sulfone, tetramethylsulfone and hexamethyl phosphoric acid triamide. Mixtures of polar solvents can be used.

Applicant's copending application, which was filed on the same day and which is entitled "Process For the Production Of p-(N-methyl)-Aminobenzoyl-L-glutamic Acid", is incorporated herein by reference, particularly the portions involving the production of p-(N-methyl)-aminobenzoyl-L-glutamic acid.

DETAILED DESCRIPTION OF THE INVENTION

As used herein, all parts, percentages and proportions are on a weight basis, unless otherwise stated herein or obvious herefrom to one ordinarily skilled in the art.

EXAMPLE 1

Production of 2,4-diamino-6-methylpteridine:

23.8 g of 2,4,5,6-tetramino pyrimidine sulfate (0.1 mole) was suspended in 750 ml of H₂O and mixed in sequence with 16.8 g of sodium bisulfite and 26 g (0.2 mole) of 1,1-dichloroacetone. The mixture was allowed to react at 60° C. while stirring. At the same time the pH was kept constant by the addition as needed of 1 N caustic soda solution. When no further NaOH consumption was found (after 5 to 6 hours), the reaction mixture was allowed to cool to ambient temperature and was mixed with NaOH up to pH 7. The desired pteridine was obtained thereby as orange colored crystals and was isolated by filtration. The yield was 8.8 g (50 percent of theoretical) of NMR-pure 6-methyl-diaminopteridine that was free of isomers.

EXAMPLE 2

The reaction was carried out as in Example 1 but at 80° C. The yield was 10.7 g of diaminomethylpteridine (61 percent of theoretical).

EXAMPLE 3

The reaction of Example 1 was repeated, but with 30 g of $NaHSO_3$. The yield was 7.0 g of diaminomethylpteridine (40 percent of theoretical).

EXAMPLE 4

Production of 2,4-diamino-6-bromomethylpteridine:

5.5 g of 2,4-diamino-6-methylpteridine were boiled with 3.83 ml of bromine and 0.27 g of dibenzoylperoxide in 240 ml of glacial acetic acid under reflux, until no further bromine could be detected (about three hours). Then the evaporated to dryness and the solid residue from the glacial acetic acid solvent (with the use of 10 percent activated charcoal) was recrystallized. The yield was 5.4 g (51 percent of theoretical) of the hydrobromide salt of the 6-bromomethyl diaminopteridine bromide as yellow crystals. The product still contained according to the NMR, about 5 percent of 6-dibromomethyldiaminopteridine and about 3 percent of 6-methyldiaminopteridine.

EXAMPLE 5

Example 4 was repeated, however, only 1.9 ml of bromine was used. After processing as in the above example, 6.8 g of yellow crystals were obtained, which according to NMR contained no 6-dibromomethyl-diaminopteridine but did 60 percent of the hydrobromide of 6-methyldiaminopteridine.

EXAMPLE 6

Example 4 was repeated, at the same time however 7.9 g of 33 percent HBr in $CH_3COOH$ were used in the mixture prior to bromation. After reprocessing, a product (5.7 g, which corresponds to 54 percent of theoretical) was obtained. The product, according to NMR, contained about 5 percent of 6-methyldiaminopteridine and 15 percent of 6-dibromomethyldiaminopteridine as by-products.

EXAMPLE 7

Production of methotrexate:

9.0 g (0.02 mole) of p-(N-methyl)-aminobenzoyl-L-glutamic acid, as the barium salt dihydrate, and 6.8 g of 6-bromomethylpteridine hydrobromide from Example 5 (0.008 mole) was stirred for about 48 hours at ambient temperature (pH=4) in 750 ml of $H_2O$, which contained 6 g of NaOH and 3.6 g of glacial acetic acid. Methotrexate resulted (3 g of yellow crystals; 83 percent of theory) which according to DC still contained traces of 6-methylpteridine. For purification, the product was suspended in 800 of ml $H_2O$ and the suspension was adjusted with 1 N NaOH to pH 11. After treatment with 4 g of activated charcoal, the solution was adjusted to pH 4 by use of concentrated $H_2SO_4$, whereupon pure methotrexate precipitated in the form of yellow crystals (2.8 g of yellow crystals; 63 percent of theoretical). The product was pure according to NMR and DC. According to DC-electrophoresis, the product contained <1 percent of pteridine. $[\alpha]_{20}{}^D$ in 0.1 N NaOH = +19.3°. (The specific rotation $[\alpha]_{20}{}^D$ in 0.1 N NaOH amounted to +19.3°.)

EXAMPLE 8

3.4 g (0.009 mole) of the 2,4-diamino-6-bromomethylpteridine hydrobromide from Example 4 was stirred overnight at ambient temperature with 4.5 g (0.01 mole) of the barium salt dihydrate of p-(N-methyl)-aminobenzoyl-L-glutamic acid in 100 ml of a mixture of DMF and $H_2O$ (1 to 1 according to volume). After that the pH of the solution was adjusted to pH 4 by means of diluted HCl. The mixture was evaporated to dryness under vacuum. The residue was absorbed (received) in 100 ml of $H_2O$. The mixture was stirred for 15 minutes at ambient temperature and then was filtered. The filtration residue was dried at 100° C. under house vacuum. Methotrexate was obtained in the form of yellow crystals, which still contained, according to NMR, about 7 percent of dimethylformamide. After purification according to Example 7, 3.6 g (87.5 percent) of L-methotrexate was obtained as yellow crystals (>99 percent purity according to DC-electrophoresis).

EXAMPLE 9

Example 8 was repeated, however, p-(N-methyl)-aminobenzoyl-L-glutamic acid, as such, was added and then neutralized by means of NaOH, prior to mixing with the pteridine compound. After reaction and processing as in Example 8, 2.8 g (68 percent) of pure methotrexate was obtained.

What is claimed is:

1. The process for the production of methotrexate, which is N[p-([2,4-diamino-6-pteridyl)-methyl]-N[10]-methylamino)-benzoyl]-L-glutamic acid and which has the formula:

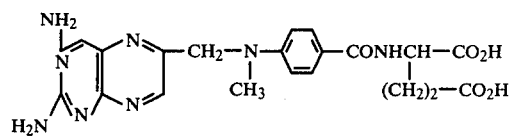

which comprises the steps of:
(a) converting 1,1-dichloroacetone with 2,4,5,6-tetraaminopyrimidine in the presence of sodium bisulfite and water at a constant pH between 3.5 and 5 and at a temperature between 10° and 100° C., 2,4-diamino-6-methylpteridine forming;
(b) converting 2,4-diamino-6-methylpteridine in a reaction medium with bromine, the reaction medium being water, 60 percent hydrogen bromide, glacial acetic acid or trifluoroacetic acid, 0.3 to 1.0 ml of bromine being used per 1.0 g of the 2,4-diamino-6-methylpteridine, 2,4-diamino-6-bromomethyl pteridine forming; and
(c) converting the 2,4-diamino-6-bromo-methyl pteridine with p-(N-methyl)-aminobenzoyl-L-glutamic acid or a salt thereof in a polar reaction medium into methoxtrexate, the polar reaction medium being water, dimethyl formamide, dimethyl acetamide, dimethyl sulfoxide, ethanol, diethyl sulfoxide, ethyleneglycoldialkylether, formamide, methyl propionamide, sulfolane, N-methyl formamide, dimethyl sulfone, tetramethylsulfone, hexamethyl phosphoric acid triamide and a mixture of at least two of such polar reaction media.

2. The process as in claim 1 wherein, in step (a), the 1,1-dichloroacetone is converted with 2,4,5,6-tetraaminopyrimidine, in the presence of 1 to 4 moles of the sodium bisulfite per mole of 2,4,5,6-tetraminopyrimidine, the pH is kept constant by addition as needed, of a diluted base, 1 to 3 moles of 1,1-dichloroacetone is used per mole of 2,4,5,6-tetraminopyrimidine, and 3 to 25 liters of water are used per mole of 2,4,5,6-tetraminopyrimidine.

3. The process as claimed in claim 2 wherein 6 to 8 liters of water are used per mole of the 2,4,5,6-tetraaminopyrimidine.

4. The process as claimed in claim 2 wherein the temperature is between 60° and 80° C.

5. The process as claimed in claim 2 wherein 2 moles of 1,1-dichloroacetone is used per mole of 2,4,5,6-tetraaminopyrimidine.

6. The process as claimed in claim 2 wherein 1.5 to 1.8 mole of the sodium bisulfite is used per mole of 2,4,5,6-tetraaminopyrimidine.

7. The process as claimed in claim 2 wherein the constant pH is 4.

8. The process as claimed in claim 2 wherein the diluted base is a dilute aqueous solution of NaOH, NaHCO$_3$ or NH$_4$OH.

9. The process as claimed in claim 2 wherein, in step (b), the 2,4-diamino-6-methylpteridine is converted with the bromine at reflux temperature in the reaction medium, 7 to 9 liters of reaction medium are used per mole of 2,4-diamino-6-methylpteridine.

10. The process as claimed in claim 9 wherein the reaction medium is glacial acetic acid.

11. The process as claimed in claim 10 wherein 0.7 ml of bromine is used per 1.0 g of 2,4-diamino-6-methylpteridine.

12. The process as claimed in claim 2 wherein, in step (c), the 2,4-diamino-6-bromo-methylpteridine is converted with the p-(N-methyl)-aminobenzoyl-L-glutamic acid or the barium salt of p-(N-methyl)-aminobenzoyl-L-glutamic acid at ambient temperature in a polar reaction medium, which is water, dimethylformamide, dimethylacetamide or a mixture of two or more of such polar reaction media, in the presence of a soluble base, 10 to 100 parts by weight of the reaction medium are used per one part by weight of (i) the 2,4-diamino-6-bromo-methylpteridine and (ii) the p-(N-methyl)-aminobenzoyl-L-glutamic acid or the barium salt of p-(N-methyl)-aminobenzoyl-L-glutamic acid.

13. The process as claimed in claim 2 wherein the reaction medium is a mixture of equal volumes of water and dimethylformamide.

14. The process as claimed in claim 2 wherein the soluble base is NaOH or NaHCO$_3$.

* * * * *